United States Patent
Howard, III et al.

(10) Patent No.: US 6,180,409 B1
(45) Date of Patent: Jan. 30, 2001

(54) SPECTROPHOTOMETRIC APPARATUS WITH MULTIPLE READHEADS

(75) Inventors: Willis E. Howard, III; Gary E. Rehm; Gerald H. Shaffer, all of Elkhart, IN (US)

(73) Assignee: Bayer Corporation, Elkhart, IN (US)

( * ) Notice: Under 35 U.S.C. 154(b), the term of this patent shall be extended for 0 days.

(21) Appl. No.: 09/170,270

(22) Filed: Oct. 13, 1998

(51) Int. Cl.$^7$ .......................... G01N 21/13; G01N 35/02
(52) U.S. Cl. .................. 436/46; 436/47; 436/169; 422/65; 422/82.05
(58) Field of Search .................. 422/65, 82.05, 422/82.08; 436/46, 47, 169, 172; 356/445, 446, 222

(56) References Cited

U.S. PATENT DOCUMENTS

| | | | |
|---|---|---|---|
| 3,907,503 | 9/1975 | Betts et al. | 23/253 R |
| 4,689,202 | 8/1987 | Khoja et al. | 422/65 |
| 4,755,058 | 7/1988 | Shaffer | 356/408 |
| 4,820,491 | 4/1989 | Khoja et al. | 422/63 |
| 5,028,139 | 7/1991 | Kramer et al. | 356/446 |
| 5,055,261 | * 10/1991 | Khoja et al. | 422/64 |
| 5,059,394 | 10/1991 | Phillips et al. | 422/68.1 |
| 5,165,078 | 11/1992 | Hough et al. | 359/233 |
| 5,231,576 | 7/1993 | Suzuki et al. | 364/413.09 |
| 5,246,858 | 9/1993 | Arbuckle et al. | 436/8 |
| 5,250,262 | 10/1993 | Heidt et al. | 422/64 |
| 5,272,518 | 12/1993 | Vincent | 356/405 |
| 5,661,563 | 8/1997 | Howard et al. | 356/446 |
| 5,701,181 | 12/1997 | Boiarski et al. | 356/446 |
| 6,027,692 | * 2/2000 | Galen et al. | 422/82.05 |

OTHER PUBLICATIONS

Clinitek 50 User's Guide, 1996 Bayer Corporation, 30 pages, Mar. 1996.

W. E. Howard, III, "An Introduction To Reflectance Spectroscopy For Dry Phase Reagent Chemistry", Miles Science Journal, pp. 33–37.

* cited by examiner

*Primary Examiner*—Jeffrey Snay
(74) *Attorney, Agent, or Firm*—Jerome L. Jeffers

(57) ABSTRACT

An apparatus for inspecting a reagent strip (14) having a fluid sample disposed thereon is provided with a conveyor system (80) adapted to move the reagent strip (14) from a first reagent strip inspection location to a second reagent strip inspection location, a first readhead (60) associated with the first reagent strip inspection location, and a second readhead (62) associated with the second reagent strip inspection location. Each of the readheads (60, 62) has a light source (64, 68) and a light detector (66, 70) associated therewith, each light source (64, 68) being adapted to illuminate the reagent strip (14) at one of the reagent strip inspection locations and each light detector (66, 70) being adapted to detect light from the reagent strip (14) when the reagent strip (14) is disposed at one of the reagent strip inspection locations.

17 Claims, 11 Drawing Sheets

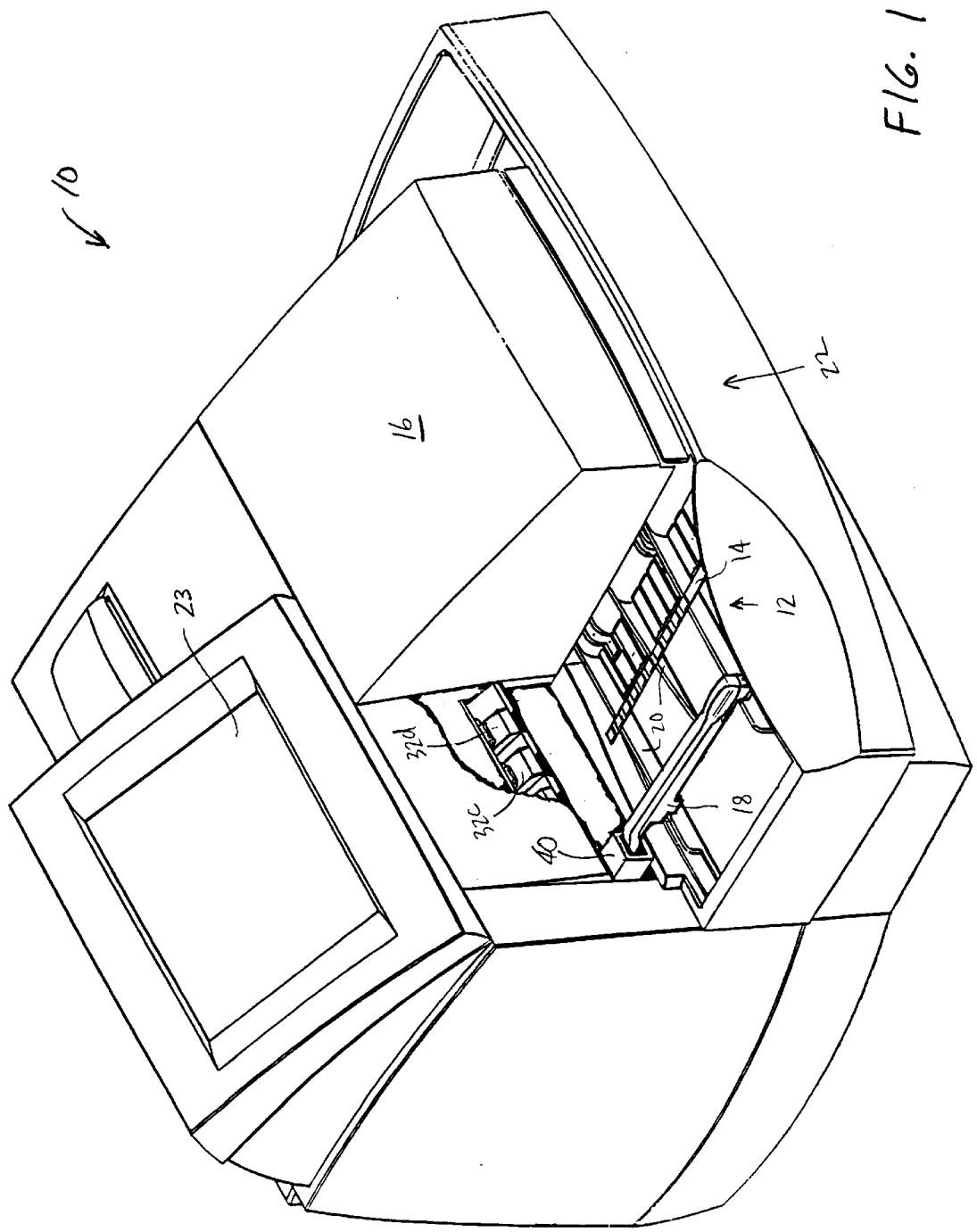

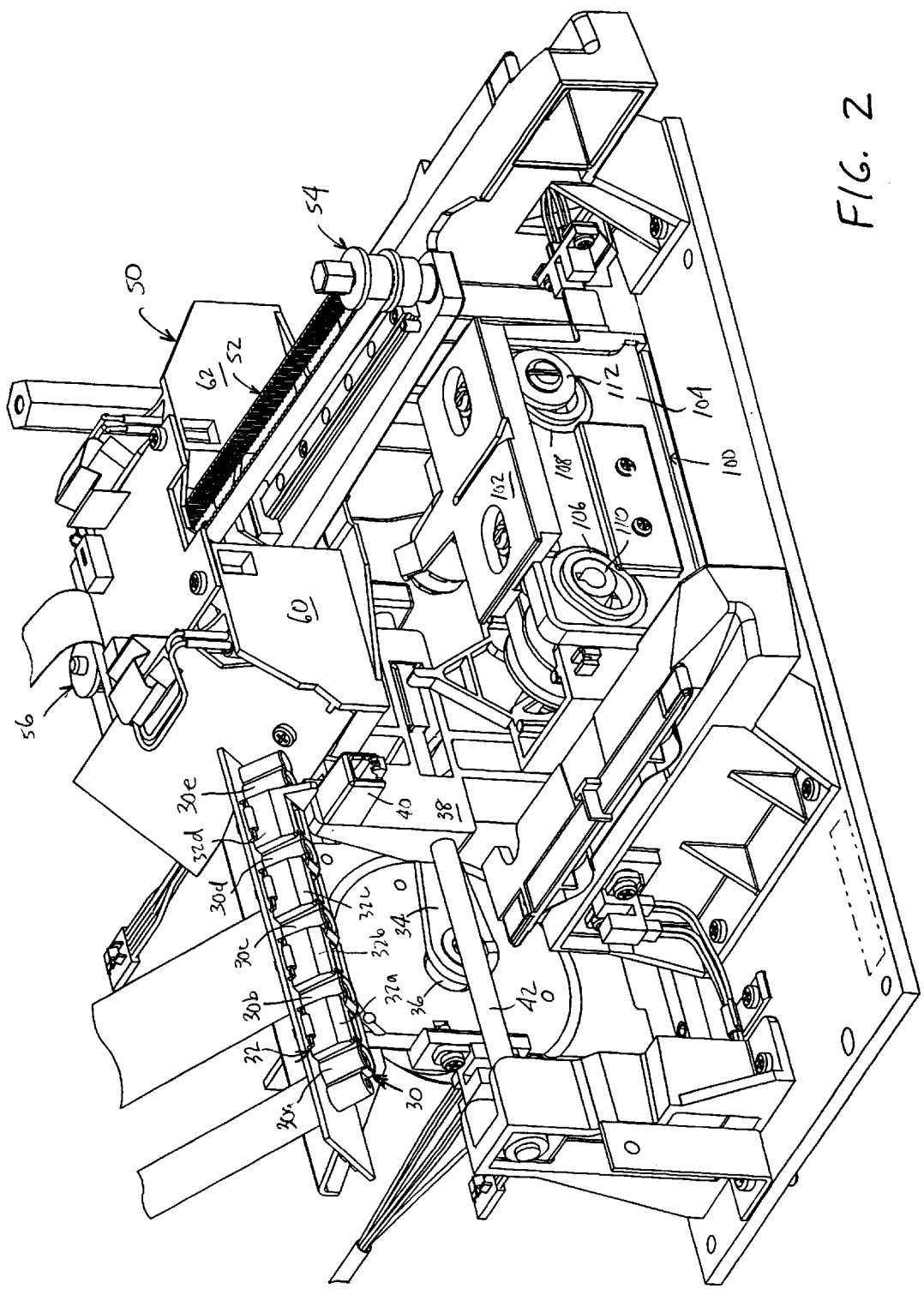

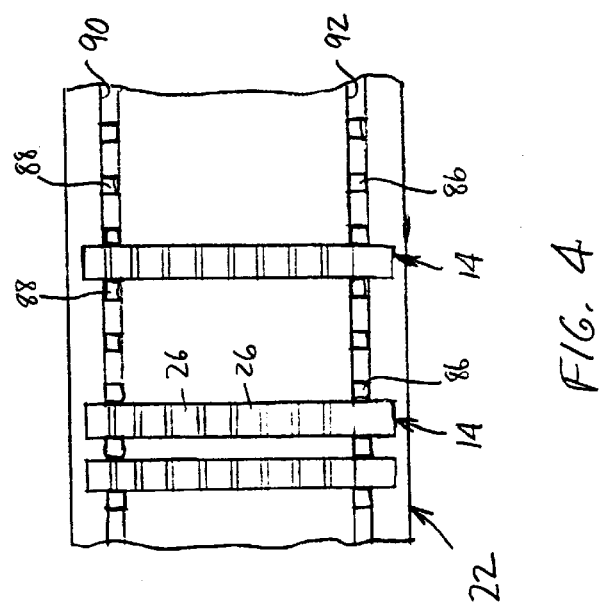
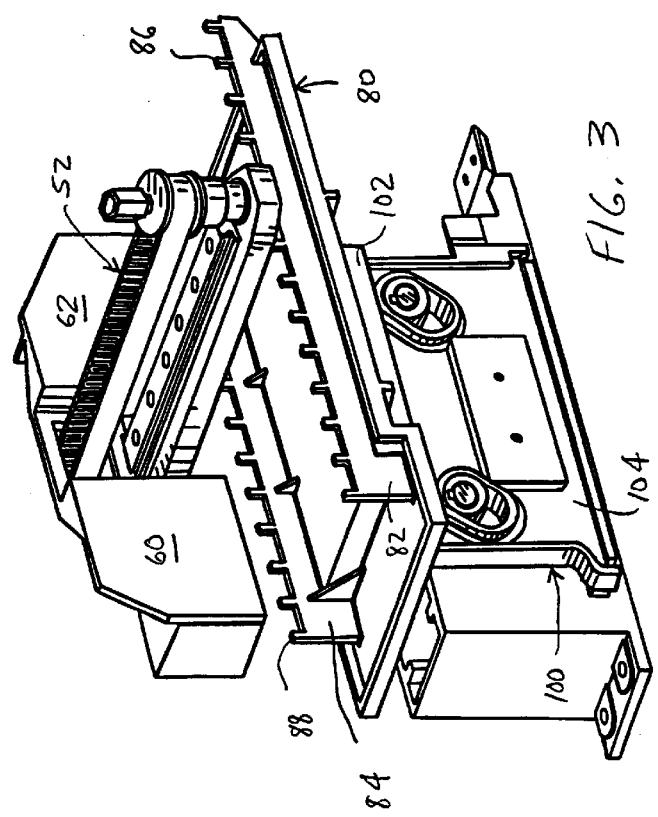

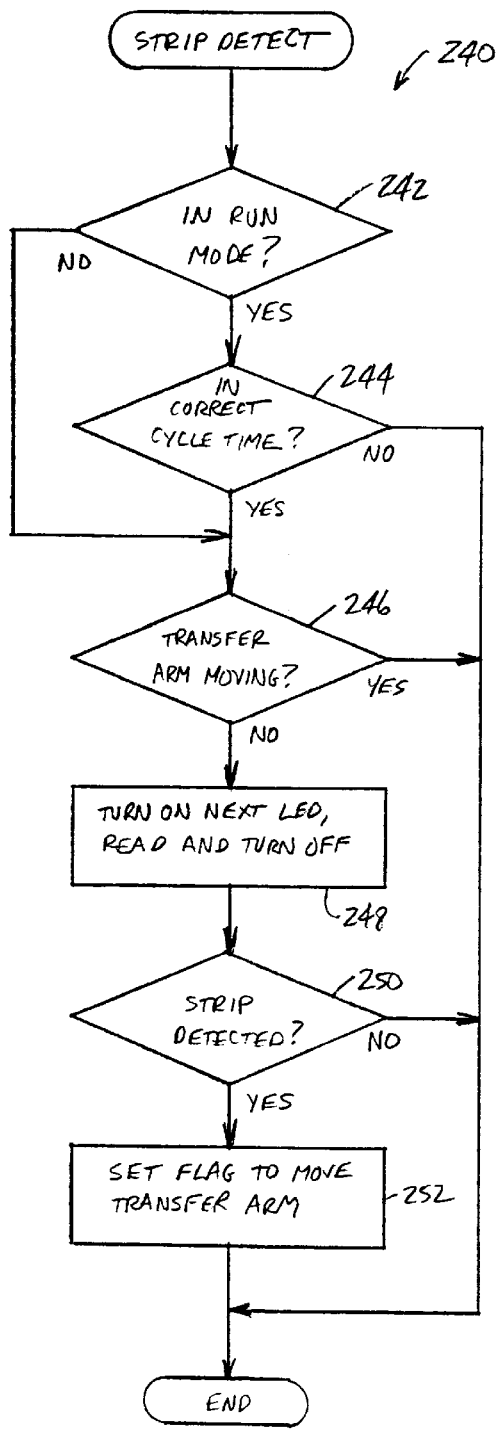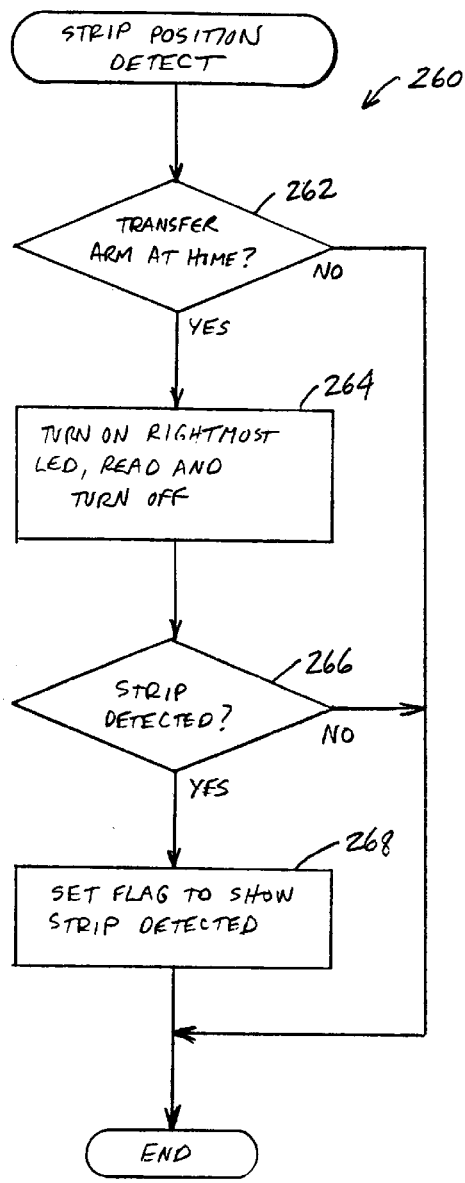
FIG. 8
FIG. 9

SPECTROPHOTOMETRIC APPARATUS WITH MULTIPLE READHEADS

BACKGROUND OF THE INVENTION

The present invention relates to an apparatus and method for performing tests on a sample of body fluid to be analyzed, and more particularly to a spectrophotometer having multiple readheads and a method for analyzing a reagent strip using multiple readheads.

It is useful for various medical diagnostic purposes to utilize a spectrophotometer to analyze samples of body fluid, for example, to determine the color of a person's urine. A conventional spectrophotometer determines the color of a urine sample disposed on a white, non-reactive pad by illuminating the pad and taking a number of reflectance readings from the pad, each having a magnitude relating to a different wavelength of visible light. The color of the urine on the pad may then be determined based upon the relative magnitudes of red, green and blue reflectance signals.

Conventional spectrophotometers may be used to perform a number of different urinalysis tests utilizing a reagent strip on which a number of different reagent pads are disposed. Each reagent pad is provided with a different reagent which causes a color change in response to the presence of a certain type of constituent in urine, such as leukocytes (white blood cells) or red blood cells. Such a reagent strip may have ten different types of reagent pads.

U.S. Pat. No. 4,689,202 to Khoja, et al. discloses a reagent test strip reading instrument having a pair of readheads adapted to optically inspect reagent strips and a conveyor system that transports reagent strips to the readheads. In the Khoja, et al. system, the readheads are adapted to read different, predetermined portions of a reagent strip. In particular, as described in column 11, lines 15–21 of the Khoja, patent, the fiber optics for reading the seven test areas on a reagent strip having a shorter incubation time are mounted on readhead 124 in position for alignment with such areas, and the fiber optics for reading the reagent test areas having the relatively longer incubation time are mounted on the readhead 125 in position for alignment with those areas.

SUMMARY OF THE INVENTION

In one aspect, the invention is directed to an apparatus for inspecting a reagent strip after the reagent strip has been contacted with fluid sample which is provided with a conveyor system adapted to move the reagent strip from a first reagent strip inspection location to a second reagent strip inspection location, a first readhead associated with the first reagent strip inspection location and adapted to optically inspect a plurality of reagent pads of the reagent strip, and a second readhead associated with the second reagent strip inspection location and adapted to optically inspect a plurality of reagent pads of the reagent strip, including at least one of the reagent pads that was optically inspected by the first readhead. Each of the readheads has a light source and a light detector associated therewith, each light source being adapted to illuminate the reagent strip at one of the reagent strip inspection locations and each light detector being adapted to detect light from the reagent strip when the reagent strip is disposed at one of the reagent strip inspection locations.

In another aspect, the invention is directed to an apparatus for inspecting reagent strips, each of which has a plurality of reagent pads disposed along its length and a body fluid sample disposed thereon. The apparatus includes a conveyor system adapted to move a plurality of the reagent strips to a first reagent strip inspection location and a plurality of the reagent strips to a second reagent strip inspection location, a first readhead associated with the first reagent strip inspection location, a second readhead associated with the second reagent strip inspection location, and a readhead positioning system operatively coupled to the first and second readheads. The readhead positioning system is adapted to selectively position the first readhead so that the first readhead inspects a plurality of the reagent pads disposed on the first reagent strip when the first reagent strip is disposed at the first inspection location, and the readhead positioning system is adapted to selectively position the second readhead so that the second readhead inspects a plurality of the reagent pads disposed on the second reagent strip when the second reagent strip is disposed at the second inspection location.

The invention is also directed to a method of automatically processing a reagent strip having a body fluid sample disposed thereon which includes the following steps: (a) automatically moving the reagent strip to a first reagent strip inspection location; (b) positioning a first readhead relative to the reagent strip when the reagent strip is at the first inspection location; (c) detecting light received from the reagent strip while the reagent strip is being illuminated at the first inspection location; (d) storing signals relating to the amount of light detected from the reagent strip when the reagent strip was positioned at the first inspection location in a memory; (e) automatically moving the reagent strip to a second reagent strip inspection location; (f) positioning a second readhead relative to the reagent strip when the reagent strip is at the second inspection location; (g) detecting light received from the reagent strip while the reagent strip is being illuminated at the second inspection location; and (h) storing signals relating to the amount of light detected from the reagent strip when the reagent strip was positioned at the second inspection location in a memory.

Where the reagent strip is provided with a plurality of reagent pads disposed along its length, step (b) may include the step of successively positioning the first readhead over a plurality of the reagent pads of the reagent strip, step (c) may include the step of detecting light received from a plurality of the reagent pads of the reagent strip while the reagent strip is being illuminated at the first inspection location, and step (d) may include the step of storing signals relating to the amount of light detected from the plurality of reagent pads of the reagent strip when the reagent strip was positioned at the first inspection location in a memory.

The features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIG. 1 is a perspective view of a spectrophotometer which may be used to perform various tests of a body fluid sample disposed on a reagent strip;

FIG. 2 is a perspective view of an internal mechanical portion of the spectrophotometer of FIG. 1;

FIG. 3 is a perspective view of an internal mechanical portion of the spectrophotometer of FIG. 1;

FIG. 4 is a top view of a reagent strip tray shown in perspective in FIG. 3;

FIG. 8 is a flowchart of a strip detect software routine performed during operation of the spectrophotometer;

FIG. 9 is a flowchart of a strip position detect software routine performed during operation of the spectrophotometer;

DETAILED DESCRIPTION OF A PREFERRED EMBODIMENT

Figure 5:
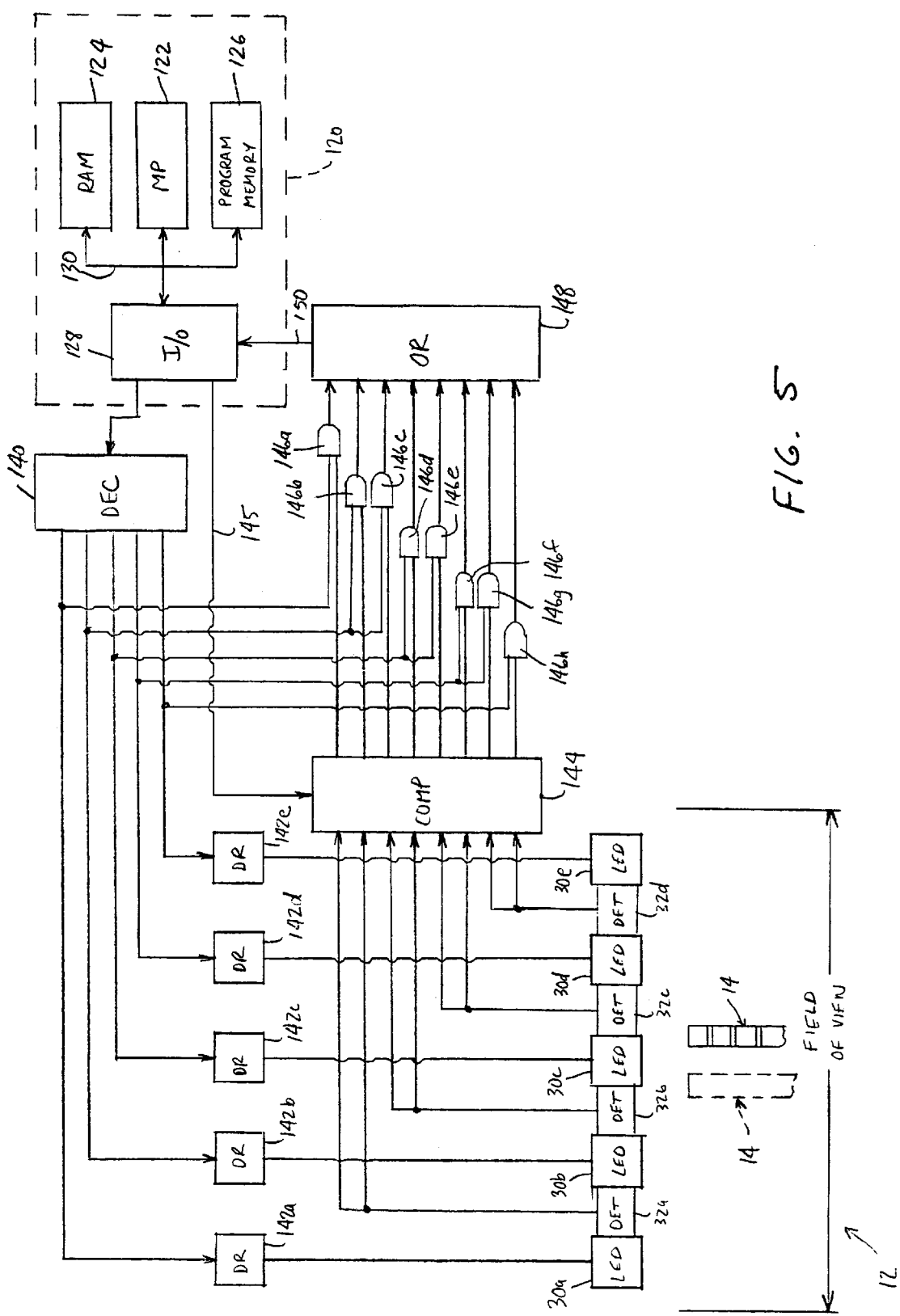
FIG. 5 is a block diagram of a first electronics portion of the spectrophotometer of FIG. 1.

FIG. 1 illustrates a spectrophotometer 10 for performing various tests, such as urinalysis tests, on reagent strips. The spectrophotometer 10 has a receiving area 12 at which a reagent strip 14 may be placed and a reagent strip inspection area covered by a housing portion 16. The reagent strip receiving area 12 is located between a laterally movable transfer arm 18 and the left side of the housing portion 16. The reagent strip 14 is supported by a number of relatively thin wall portions 20 formed in the left-hand side of a reagent strip support table 22.

To operate the spectrophotometer 10, the reagent strip 14 may be placed anywhere in the receiving area 12. The spectrophotometer 10 automatically detects the presence of the reagent strip 14, and upon such detection, causes the transfer arm 18 to move from left to right in FIG. 1, thus automatically moving the reagent strip 14 from the receiving area 12 to the inspection area located within the housing portion 16. The spectrophotometer 10 includes a visual display 23 for displaying various messages relating to the operation of the spectrophotometer 10.

Figure 6:
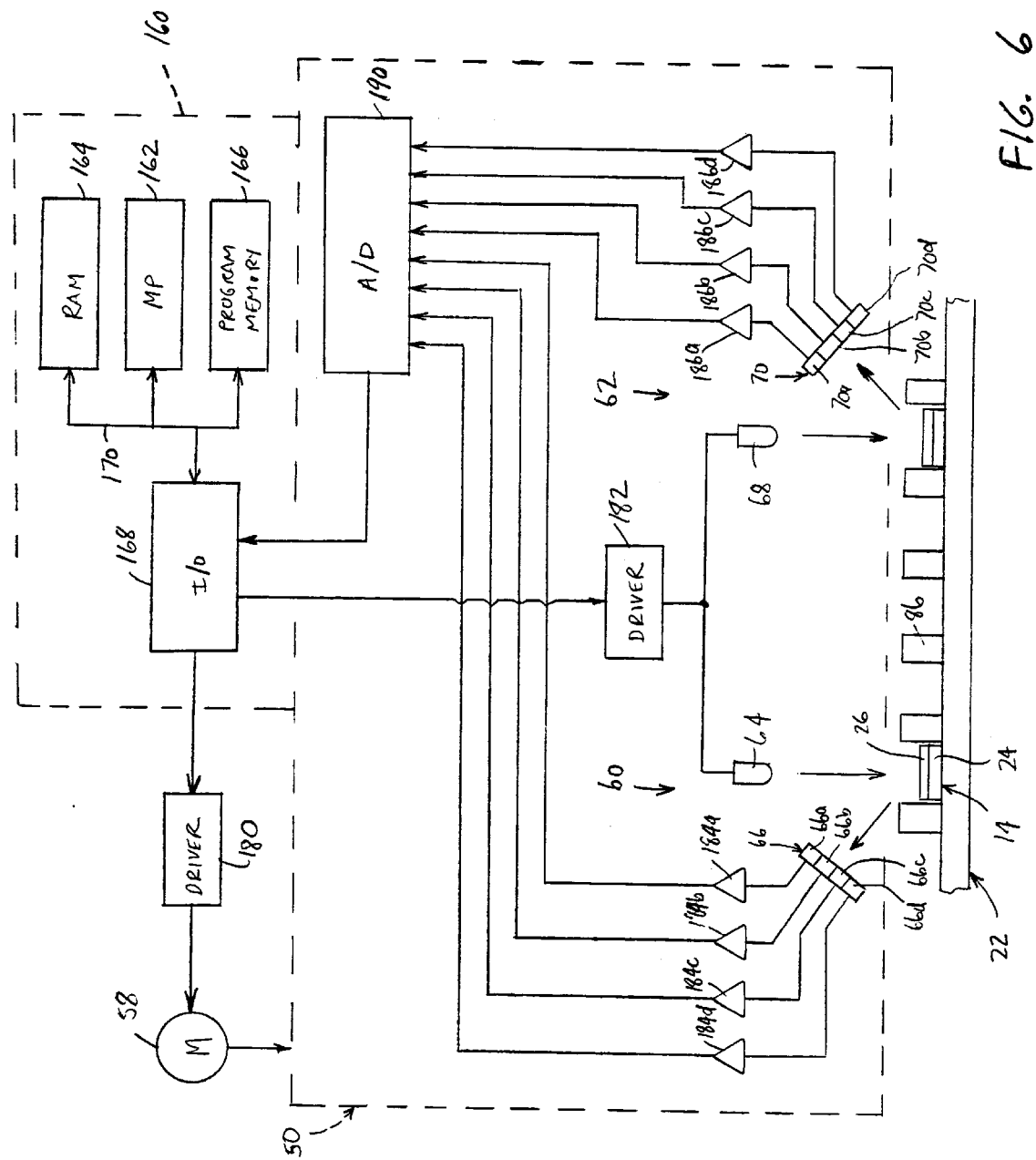
FIG. 6 is a block diagram of a second electronics portion of the spectrophotometer of FIG. 1.

As shown in FIGS. 1, 4 and 6, the reagent strips 14 used in the spectrophotometer 10 have a thin, non-reactive substrate 24 on which a number of reagent pads 26 are fixed. Each reagent pad 26 is composed of a relatively absorbent material impregnated with a respective reagent, each reagent and reagent pad 26 being associated with a particular test to be performed. When urinalysis tests are performed, they may include, for example, a test for leukocytes in the urine, a test of the pH of the urine, a test for blood in the urine, etc. When each reagent pad 26 comes into contact with a urine sample, the pad changes color over a time period, depending on the reagent used and the characteristics of the urine sample. The reagent strip 14 may be, for example, a Multistix® reagent strip commercially available from Bayer Corporation.

Mechanical Structure

FIG. 2 is a perspective view of the interior mechanical structure of the spectrophotometer 10. Referring to FIG. 2, the spectrophotometer 10 includes a light emitting apparatus 30, which may be provided in the form of five light-emitting diodes (LEDs) 30a–30e, which may be in the form of narrow angle, high output LEDs commercially available from Hewlett Packard. The LEDs 30a–30e may be spaced apart so that each of them illuminates a separate portion of the reagent strip receiving area 12. The spectrophotometer 10 includes a detecting apparatus 32, which may be in the form of four light detectors 32a–32d, each of which is disposed between two of the LEDs 30a–30e. The detectors 32a–32d are positioned so that they detect light which is received from portions of the receiving area 12 which are illuminated by the LEDs 30a–30e.

As shown in the left-hand portion of FIG. 2, the spectrophotometer 10 includes a pivot arm 34 having a central portion which is connected to a rotatable shaft 36, which is controllably driven by a motor (not shown). The end of the pivot arm 34 is slidably disposed in a vertical shaft formed in the back of a transfer arm support member 38 to which the transfer arm 18 (FIG. 1) is connected. The transfer arm support member 38, which has a receptacle 40 in which an end of the transfer arm 18 is disposed, is slidably supported by a horizontally disposed cylindrical rod 42. The horizontal position and movement of the transfer arm 18 is controlled by selectively causing the pivot arm 34 to rotate about the central shaft 36 to change the lateral position of the end of the pivot arm 34, and thus the lateral position of the transfer arm support member 38.

As shown in the right-hand portion of FIG. 2, the spectrophotometer 10 has a movable carriage 50 that is fixed to one side of a positioning belt 52 supported by a pair of toothed gears 54, 56. The gear 56 is fixed to a rotatable drive shaft (not shown) that is controllably driven by a motor 58 (FIG. 6) to precisely move and position the movable carriage 50 in a direction parallel to the length of the reagent strip 14 (FIG. 1). Although a positioning system in the form of gears 54, 56 and belt 52 is shown, other types of positioning systems could be utilized, such as one or more round gears which mate with a linear gear fixed to the readheads 60, 62, or any type of positioning system adapted to adjust the linear position of a device.

The movable carriage 50 has a pair of readheads 60, 62. The readhead 60 includes a light source 64 (FIG. 6), which may be provided in the form of an incandescent lamp, for example, and a detector 66, which may be provided in the form of four light detectors 66a–66d, each of which is adapted to detect light of a different wavelength, such as red, blue, green and infrared light, for example. The readhead 62 includes a light source 68 (FIG. 6), which may be provided in the form of an incandescent lamp, and a detector 70, which may be provided in the form of four light detectors 70a–70d, each of which is also adapted to detect light of a different wavelength. Although the readheads 60, 62 could be designed as disclosed in U.S. Pat. No. 5,661,563 to Howard, et al., which is incorporated by reference herein, no particular design of the readheads 60, 62 is considered necessary to the invention. The light sources 64, 68 could be other than incandescent light sources, and the detectors 66, 70 could be designed to detect light of only a single wavelength.

FIG. 3 is a perspective view of a portion of the spectrophotometer 10 which shows a reagent strip advancing tray 80. The advancing tray 80 has a pair of upwardly extending ribs 82, 84. The upper portion of the rib 82 has a plurality of pegs 86 extending therefrom, and the upper portion of the rib 84 has a plurality of pegs 88 extending therefrom. The pegs 86, 88 are spaced apart by a distance slightly greater than the width of the reagent strip 14 so that the space between each adjacent pair of pegs 86, 88 can accommodate one of the reagent strips 14. Referring to FIG. 4, the pegs 86, 88 of the advancing tray 80 may extend upwardly through a pair of slots 90, 92 formed in the reagent strip support table 22.

The reagent strip advancing tray 80 is supported by a positioning mechanism 100 which is shown in FIGS. 2 and 3. The positioning mechanism 100 has a support table 102 which supports the reagent strip advancing tray 80 and a mechanism for moving the support table 102 in a generally circular path which includes a vertical member 104 having a pair of oblong slots 106, 108 formed therein and a pair of motor-driven actuators 110, 112 disposed within the slots 106, 108. Rotation of the actuators 110, 112 causes the vertical member 104 and the support table 102 to move in a circular path, as disclosed in U.S. Pat. No. 4,689,202, which is incorporated by reference herein.

The movement of the support table 102 causes the advancing tray 80 to move in a circular path, which in turn moves the pegs 86, 88 to cause the reagent strips 14 disposed between them to be periodically moved or indexed rightward through the spectrophotometer 10, so that a reagent strip 14 is disposed at a first reagent strip inspection position beneath the readhead 60, and then is disposed at a second reagent strip inspection position beneath the readhead 62.

Referring to FIG. 4, when the advancing tray 80 moves in a single circular path, the pegs 86, 88 move from left to right while they extend upwardly through the reagent strip support table 22, thus moving each of the reagent strips 14 one reagent strip position to the right. During the latter half of the circular motion, the pegs 86, 88 are downwardly retracted so that their upper ends are disposed beneath the upper surface of the support table 22, so that they can be moved from right to left without moving the reagent strips 14. The particular design of the system for conveying the reagent strips 14 from the receiving area 12 to the inspection area within the housing portion 16 and for conveying the reagent strips 14 within the inspection area is not considered necessary to the invention, and other types of conveyor systems could be utilized.

Electronics

FIG. 5 is a block diagram of the electronics and other components of the spectrophotometer 10 which relate to the automatic detection of a reagent strip 14 at the reagent strip receiving area 12. Referring to FIG. 5, the automatic detection of a reagent strip 14 is controlled by a controller 120 which has a microprocessor 122, a random-access memory (RAM) 124, a program memory 126, and an input/output (I/O) circuit 128, all of which are interconnected via an address/data bus 130.

The controller 120 selectively applies power to the LEDs 30a–30e via a decoder circuit 140 which is connected to five driver circuits 142a–142e, each of which is connected to cause a respective one of the LEDs 30a–30e to be turned on. The LEDs 30a–30e may be turned on periodically, one at a time, so that separate overlapping portions of the reagent strip receiving area 12 are successively illuminated.

The detectors 32a–32d are positioned to detect light from separate overlapping portions of the receiving area 12, which overlapping portions generally make up the field of view of the detecting apparatus 32, as shown in FIG. 5. Each of the detectors 32a–32d generates an illumination signal having a magnitude corresponding to the amount of light detected. Each of those illumination signals is transmitted to a programmable comparator circuit 144, which compares each of the illumination signals to a respective one of eight thresholds, as described below, to determine whether a reagent strip 14 is present in the reagent strip receiving area 12. The thresholds may be transmitted to the comparator 144 via a line 145.

The comparator 144 generates eight output signals, each output signal having a value (i.e. logic "0" or logic "1") corresponding to whether the associated illumination signal was greater than its associated threshold. Those eight output signals may be provided to a selection circuit, which may be in the form of eight AND gates 146a–146h, to enable certain of the output signals and disable the rest. Only one of the five outputs of the decoder 140 is activated, or logic "1," at a time, in order to turn on exactly one of the LEDs 30a–30e at a time. Each of those five outputs is transmitted to either one or two of the AND gates 146a–146h in order to enable either one or two of the AND gates 146a–146h and to disable the rest.

In particular, a logic "0" output of the decoder 140, will force the output of the AND gate(s) to which it is supplied to have a logic "0" value, thus preventing the detection signal(s) provided to such AND gate(s) to cause the output of the OR gate to be logic "1," representing the detection of a reagent strip 14. For example, when the LED 30a is turned on, the single logic "1" output connected to the driver circuit 142a will allow the AND gate 146a (which receives the illumination signal generated by the detector 32a) to be enabled, and the other four logic "0" outputs of the decoder 140 will effectively disable the AND gates 146b–146h.

The output signals of the AND gates 146a–146h are transmitted to an OR gate 148, which transmits a strip-detected signal to the controller 120 if any of the inputs to the OR gate 148 is logic "1," meaning that at least one of the illumination signals generated by the detectors 32a–32d was greater than its associated threshold.

FIG. 6 is a block diagram of the electronics and other components of the spectrophotometer 10 which relate to the inspection of reagent strips 14 at the reagent strip inspection positions within the housing portion 16. Referring to FIG. 6, the inspection of reagent strips 14 is controlled by a controller 160 which has a microprocessor 162, a random-access memory (RAM) 164, a program memory 166, and an I/O circuit 168, all of which are interconnected via an address/data bus 170.

The controller 160 selectively drives the motor 58, which may be a stepping motor, through a drive circuit 180, to position the carriage 50 so that each of the readheads 60, 62 is positioned over a respective one of the two reagent strip inspection locations (at which either one or two reagent strips 14 may be present). The controller 160 selectively turns on the light sources 64, 68 in the readheads 60, 62 via a drive circuit 182 and, while those light sources 64, 68 are turned on, receives illumination signals from eight amplifiers 184a–184d, 186a–186d, each of which is connected to receive the output of one of the detectors 66a–66d, 70a–70d. Those illumination signals are transmitted to an analog-to-digital (A/D) converter 190, which converts them from analog signals into digital signals and then transmits them to the controller 160, which causes signals relating to them to be stored in the RAM 164. The illumination signals may be stored in the RAM 164, or alternatively reflectance signals which are derived from the illumination signals may be stored in the RAM 164.

Automatic Detection of Reagent Strip

The automatic detection of a reagent strip 14 in the reagent strip receiving location 12 is controlled by a computer program stored in the program memory 126 of the controller 120 and executed by the microprocessor 122 (FIG. 5). That computer program includes a calibration routine 200 (FIG. 7) that is performed each time the spectrophotometer 10 is turned on, a strip detect routine 240 (FIG. 8) periodically performed to detect the placement of a reagent strip 14 at any point within the reagent strip receiving area 12, and a software routine 260 (FIG. 9) that automatically detects when the reagent strip 14 reaches a predetermined position between the reagent strip receiving location 12 and the reagent strip inspection area disposed beneath the housing portion 16.

Calibration Routine

Figure 7:
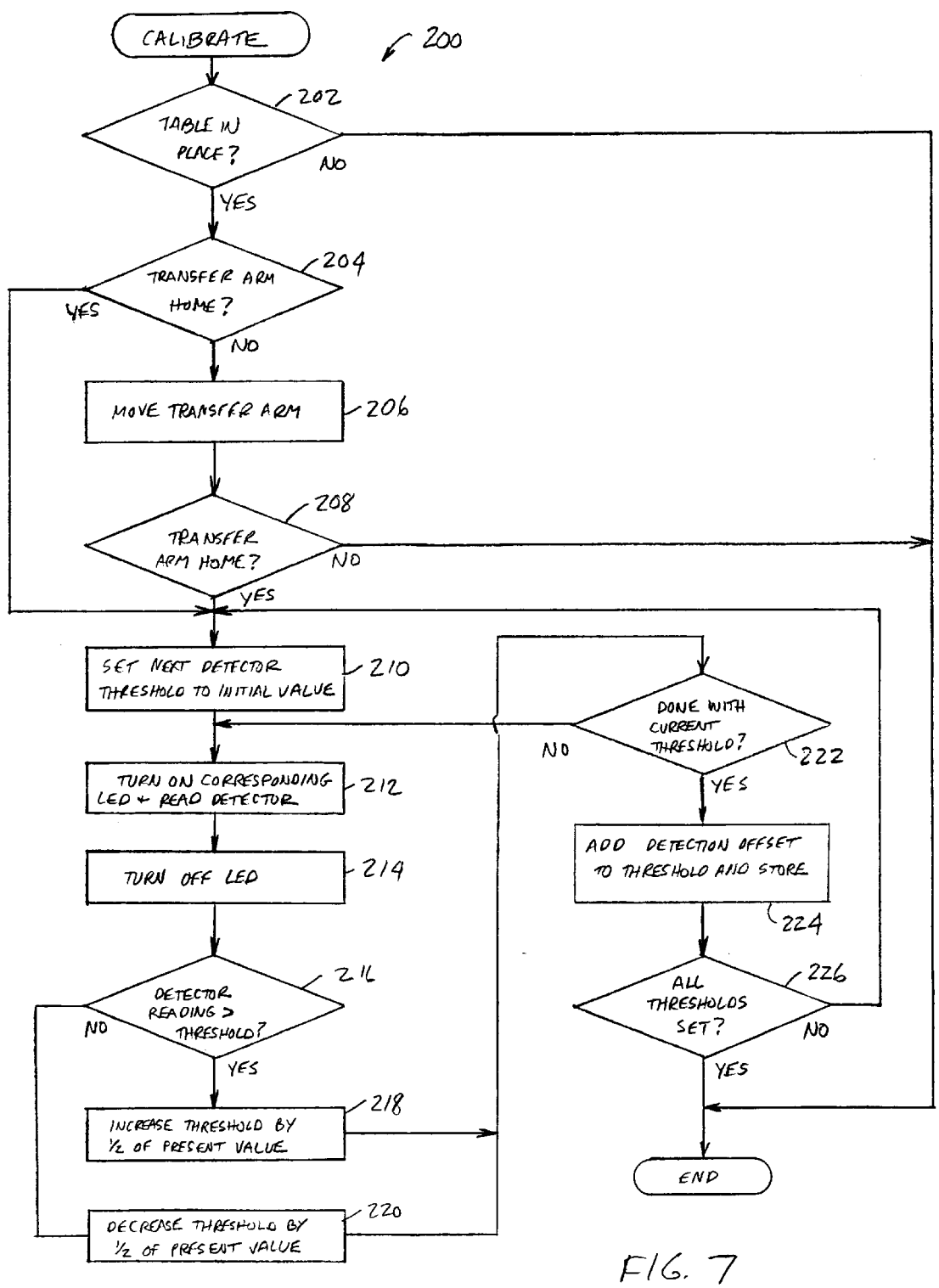
FIG. 7 is a flowchart of a calibrate software routine performed during operation of the spectrophotometer.

A flowchart of the calibration routine 200 is shown in FIG. 7. This routine 200 is performed when the spectrophotometer 10 is turned on to determine the eight thresholds used by the comparator 144 (FIG. 5) in the detection of a reagent strip 14. Referring to FIG. 7, a number of preliminary steps 202, 202, 206, 208 may be utilized to ensure that the reagent strip support table 22 (FIGS. 1 and 4), which is removable from the spectrophotometer 10, is in place and that the transfer arm 18 is at a home position and out of the field of view of the detectors 32a–32d (FIG. 5).

Each illumination signal generated by the four detectors 32a–32d used to detect the presence of a reagent strip 14 is compared with either one or two thresholds, which are determined by the routine 200. When the LED 30a disposed on the left end of the light emitting apparatus 30 is turned on, the signal generated by its adjacent detector (i.e. detector 32a) is compared with a threshold. Similarly, when the LED 30e disposed on the right end of the light emitting apparatus 30 is turned on, the signal generated by its adjacent detector (i.e. detector 32d) is compared with a threshold.

When one of the LEDs 30b–30d positioned between the LEDs 30a and 30e is turned on, the two signals generated by the two detectors disposed adjacent the powered LED are compared with two thresholds. For example, when the LED 30c is turned on, the signal generated by the detector 32b is compared with a first threshold and the illumination signal generated by the detector 32c is compared with a second threshold. This is done because a reagent strip 14 could be present at two possible locations relative to the turned on LED 30c: 1) a first location, shown in solid lines in FIG. 5, between the turned on LED 30c and the detector 32c on its right-hand side, and 2) a second location, shown in dotted lines in FIG. 5, between the turned on LED 30c and the detector 32b on its right-hand side. The reagent strip 14 is best detected in the first position via the detector 32c, and is best detected in the second position via the detector 32b.

Referring to FIG. 7, steps 210, 212, 214, 216, 218, 220, 222 and 224 are performed, without any reagent strip 14 present in the receiving area 12, to determine the eight thresholds used in the reagent strip detection process. At step 210, the next (or first) detector threshold is set to an initial value, such as 50% of the maximum range, for example. At step 212, the corresponding LED is turned on and the illumination signal generated by the associated detector is read, and at step 214 the LED is turned off (the LEDs 30a–30e may be turned on for very short time periods, such as 15 microseconds).

If the detector reading is greater than the threshold as determined at step 216, the routine branches to step 218 where the value of the threshold is increased by one-half its current value; otherwise, the routine branches to step 220 where the value of the threshold is decreased by one-half its current value. The routine then branches to step 222, which determines whether the current threshold has been finalized. This could be accomplished, for example, by performing steps 212, 214, 216, 218, 220 a predetermined number of times, such as seven times.

It should be noted that the effect of the repeated performance of even steps 212–220 is to make the threshold approximately equal to the magnitude of the illumination signal generated by the detector in the absence of a reagent strip 14.

At step 224, a detection offset is then added to the threshold determined by even steps 212–222. This detection offset is based upon the difference in the illumination signal produced by the presence of a reagent strip 14, which is white or has a relatively light color, and the color of the reagent strip support table 22, which has a relatively dark color. At step 226, if not all of the eight thresholds have been set, the routine branches back to step 210 to set the next threshold.

In the above routine, the eight thresholds are set by turning on the LEDs 30a–30e and reading their associated detectors 32a–32d as follows: 1) turning on LED 30a and reading detector 32a; 2) turning on LED 30b and reading detector 32a; 3) turning on LED 30b and reading detector 32b; 4) turning on LED 30c and reading detector 32b; 5) turning on LED 30c and reading detector 32c; 6) turning on LED 30d and reading detector 32c; 7) turning on LED 30d and reading detector 32d; and 8) turning on LED 30e and reading detector 32d. Although a particular method of calibrating the spectrophotometer 10 is described above, that particular method is not considered necessary to the invention and other methods (or no calibration method) could be used.

Strip Detect Routine

FIG. 8 is a flowchart of the strip detect routine 240, which is periodically performed, once every 100 milliseconds for example, to determine whether a reagent strip 14 has been placed in the reagent strip receiving area 12.

Referring to FIG. 8, preliminary steps 242, 244, 246 may be performed to limit the times when the spectrophotometer 10 searches for the presence of a reagent strip 14. When the spectrophotometer 10 is in its run mode, the spectrophotometer 10 has a predetermined cycle time (e.g. seven seconds in duration) which relates to its operation. At step 242, if the spectrophotometer 10 is not in the run mode, meaning that it is not operating according to its cycle time, the routine branches to step 246. If the spectrophotometer 10 is in its run mode, the routine branches to step 244 where it determines whether the spectrophotometer 10 is in a predetermined correct portion of the cycle time during which time it is appropriate to check for the presence of a reagent strip 14. This correct cycle time may be include time periods during which the transfer arm 18 is probably not moving (it is possible that a moving transfer 18 could be mistaken for a reagent strip 14) and may exclude other time periods, for example, later periods in a cycle which would not allow sufficient time for the user to place a reagent strip 14 at the receiving location 12. If the transfer arm 18 is moving as determined at step 246, the routine ends without checking for the presence of a reagent strip 14 since the moving transfer arm 18 could be mistaken for a reagent strip 14.

At step 248, the next (or first) of the LEDs 30a–30e is turned on, the one or two of the detectors 32a–32d associated with that LED is read (via the electronics as described above), and the LED is turned off. At step 250, if the illumination signal(s) generated by the detector(s) is (are) greater than the corresponding threshold(s) (as determined by the detection signal on the line 150 generated by the OR circuit 148 described above), meaning that a reagent strip 14 is detected, the routine branches to step 252, where a flag is set to subsequently cause the transfer arm 18 to automatically move, from left to right in FIG. 1, in order to move the reagent strip 14 from the reagent strip receiving area 12 to the inspection area disposed within the housing portion 16. If no reagent strip 14 is detected, the routine simply ends.

Each time the routine 240 is performed, a successive one of the LEDs 30a–30e is turned on, and the one or two adjacent detectors 32 are read to determine whether a reagent strip 14 is present.

Strip Position Detect Routine

FIG. 9 is a flowchart of a reagent strip position detect routine 260 that may be performed to detect a reagent strip 14 as it is being moved from the receiving area 12 to the inspection area within the housing portion 16. The position detect routine 260 is periodically performed (e.g. every 3 milliseconds) while the transfer arm 18 is moving. Since the transfer arm 18 is intended to move only in response to an earlier detection of a reagent strip 14 at the receiving area 12, the routine 260 acts to confirm the presence of a reagent strip 14 at the right side of the moving transfer arm 18, and thus that the presence of a reagent strip 14 caused the transfer arm 18 to begin moving, as opposed to the unintended detection of the temporary presence of someone's hand in front of one of the detectors 32a–32d, for example.

Referring to FIG. 9, at step 262, if the transfer arm 18 is at a "home" position (which may be determined by a conventional home sensor) located adjacent the right end of the receiving area 12, steps 264, 266, 268 are performed to determine whether a reagent strip 14 is present. At step 264, the rightmost LED 30e is turned on, the rightmost detector 32d is read, and the LED 30e is turned off. At step 266, if a reagent strip 14 is detected (based on comparison of the illumination signal with the corresponding threshold), the routine branches to step 268 where a flag is set to indicate that the reagent strip 14 was detected, thus confirming the presence of the reagent strip 14. The absence of the strip detected flag being set after the routine 260 is performed a predetermined number of times when the transfer arm 18 is in the home position indicates to the spectrophotometer 10 that the initial detection of the reagent strip 14 that caused the transfer arm 18 to move was spurious.

Inspection of Reagent Strip After Detection

During operation of the spectrophotometer 10, reagent strips 14 may be continually placed at the receiving location 12 by the operator, one at a time, and such reagent strips 14 will be automatically transferred inside the housing portion 16 to be optically inspected by the readheads 60, 62 at one or both of two inspection locations, one of the inspection locations being aligned with the readhead 60 and the other inspection location being aligned with the readhead 62, as shown in FIG. 6.

The inspection of reagent strips 14 is controlled by a computer program stored in the program memory 166 of the controller 160 (FIG. 6) and executed by the microprocessor 162. That computer program includes a main routine 300 (FIG. 10) that is performed during operation of the spectrophotometer 10, an initialize position routine 310 that is periodically performed to position the readheads 60, 62 over a pair of calibration chips of a known color, a calibration routine 320 that is periodically performed while the readheads 60, 62 are positioned over the calibration chips, and a read routine 330 that is performed to inspect the reagent pads 26 of the reagent strips 14 at the inspection locations.

Main Routine

Figure 10:
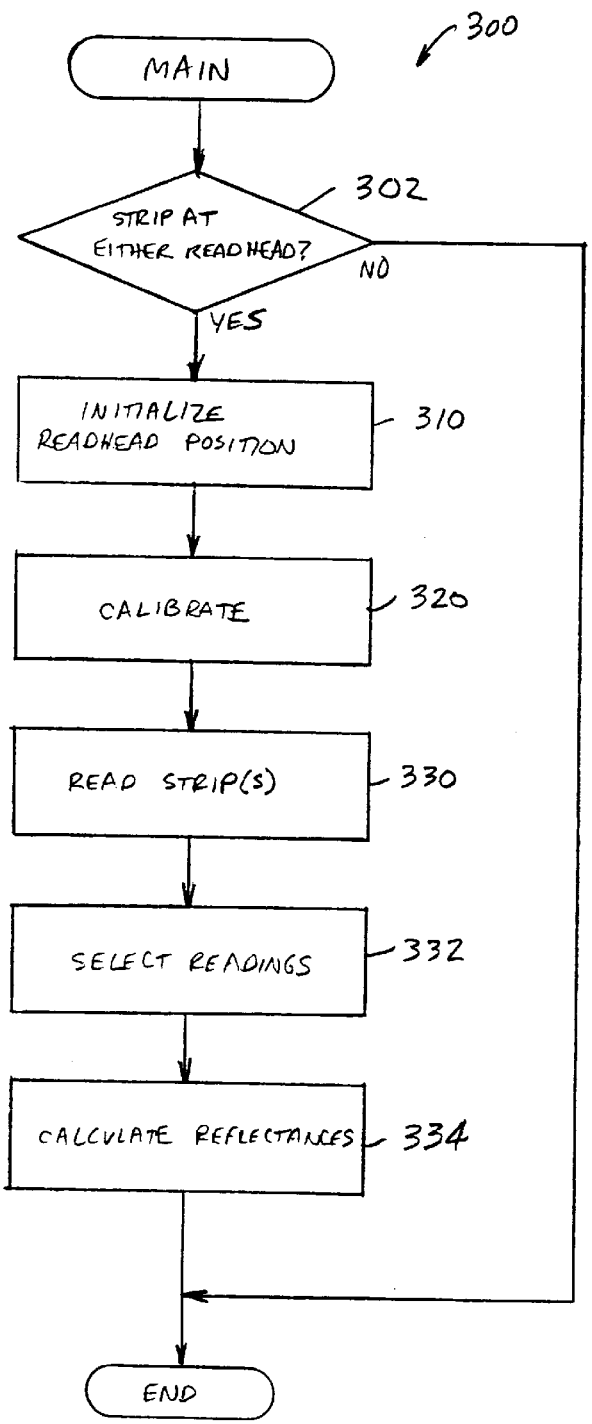
FIG. 10 is a flowchart of a main software routine performed during operation of the spectrophotometer.

Referring to flowchart of the main routine 300 shown in FIG. 10, if there is no reagent strip 14 at either of the two inspection locations as determined at step 302, the routine ends. Since the position of the reagent strips 14 may be kept track of by the controller 160 as the reagent strips 14 are fed by the transfer arm 18, the presence of a reagent strip 14 at either of the two inspection locations can be determined by the controller 160.

If there is a reagent strip 14 at one (or reagent strips 14 at both) of the inspection locations, the initialize routine 310, which causes the readheads 60, 62 to be moved to the centers of the calibration chips, is performed. The calibrate routine 320 is then performed to calibrate the detectors 66a–66d and 70a–70d of the readheads 60, 62, and then the read routine 330 causes the reagent pads 26 disposed along the length of each reagent strip 14 at an inspection location to be successively inspected by reading the illumination signals generated by the detectors 66a–66d, 70a–70d while each reagent pad 26 is illuminated by one of the light sources 64, 68.

As described below in connection with FIG. 13, the detectors 66a–66d, 70a–70d of the readheads 60, 62 are read at very close intervals, such as every 0.017 of an inch. Since the width of each of the reagent pads 26 on a reagent strip 14 is considerably wider than 0.017 of an inch, multiple sets of detector readings are generated for each reagent pad 26.

Step 332 may be performed to select which sets of the detector readings are utilized. The detector readings may be selected, for example, by determining which sets of detector readings were taken from the approximate center of each of the reagent pads 26. This could be accomplished by detecting the position of the longitudinal end of the reagent strip 14 (when the reflectance signal increases due to the detectors 66a–66d moving from the relatively dark table 22 to a relatively light reagent strip 14), and then selecting only those detector readings corresponding to predetermined distances from the end of the reagent strip 14 (based on the known widths and spacings of the reagent pads 26).

Figure 12:
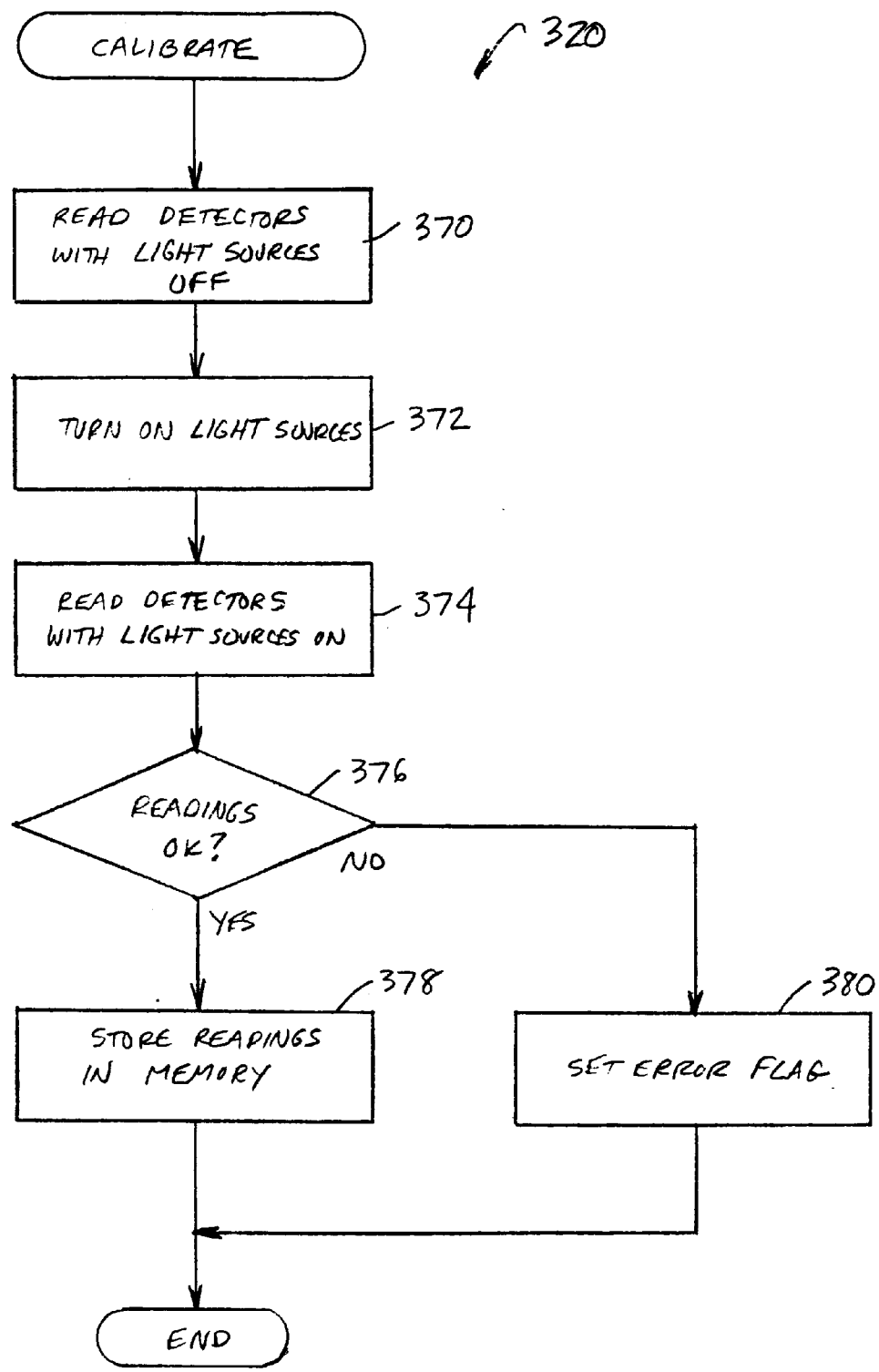
FIG. 12 is a flowchart of a calibration software routine performed during operation of the spectrophotometer.

Step 334 may be performed to transform the raw data of the detector readings into reflectance data, taking into account the dark values and the calibration values described below in connection with FIG. 12. For example, the calculated reflectance ("Reflect$_{Calc}$") could be determined in accordance with the following formula:

Reflect$_{Calc}$=% Reflectance*(Reagent−Dark)/(Calibration−Dark), where "%Reflectance" is the known reflectance percentage of the calibration chips, where "Reagent" is the raw detector reading of a reagent pad 26, and where "Dark" and "Calibration" are the dark and calibration values described below in connection with FIG. 12.

Initialize Position Routine

The purpose of the initialize position routine 310 (FIG. 11) is to position the detectors 66a–66d, 70a–70d of the readheads 60, 62 so that they are disposed over, respectively, the centers of a pair of calibration chips (not shown) of a known color which are disposed on the reagent strip support table 22.

Figure 11:
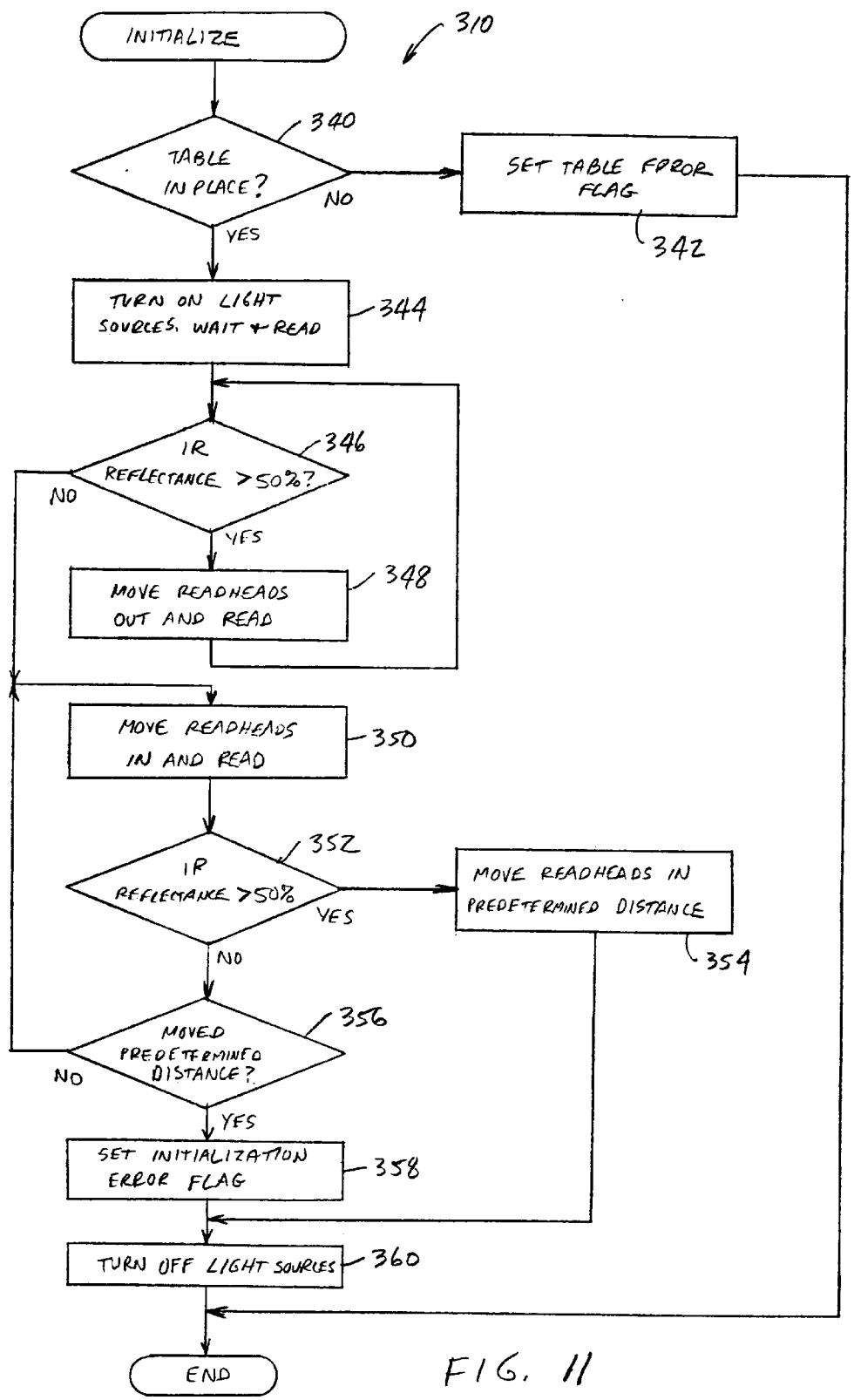
FIG. 11 is a flowchart of an initialization software routine performed during operation of the spectrophotometer.

Referring to FIG. 11, the initialize position routine 310 begins at step 340, which determines whether the reagent strip support table 22, which may be removed from the spectrophotometer 10 for cleaning purposes, is in place. If not, an error flag is set at step 342 and then the routine ends. If the table 22 is in place, the routine branches to step 344 where the light sources 64, 68 of the readheads 60, 62 are turned on, a predetermined period of time (e.g. one-half of a second) is waited, and the detectors which detect infrared (IR) radiation are read by the controller 160 (FIG. 6) via the A/D converter 190.

The purpose of even steps 346–360 is to position the readheads 60, 62 so that the detectors 66a–66d, 70a–70d are positioned over the centers of their respective calibration chips (not shown), which are relatively light in color compared with the surrounding area of the reagent strip support table 22. Thus, when the detectors 66a–66d are positioned over the calibration chips, the reflectance represented by the signals generated by the detectors 66a–66d, 70a–70d will be relatively large, e.g. over 50%.

When the routine 310 begins, the detectors 66a–66d, 70a–70d of the readheads 60, 62 are positioned somewhere over the calibration chips. The precise positioning of the detectors 66a–66d, 70a–70d over the centers of the respective calibration chips is done by steps 346 and 348, which move the readheads 60, 62 in one direction until they pass over the edges of the calibration chips (which is detected at step 346 when the percent reflectance decreases to become less than a predetermined value, such as 50%); by steps 350 and 352, which move the readheads 60, 62 back in the opposite direction until they pass over the same edges of the calibration chips (which is detected when the percent reflectance increases to become greater than a predetermined value, such as 50%), and then by step 354, which moves the readheads 60, 62 in the same direction by a predetermined distance (corresponding to onehalf the length of the calibration chips) so that the detectors 66a–66d, 70a–70d are positioned directly over the centers of the calibration chips.

Step 356 checks for an error condition (the failure of the edges of the calibration chips to be detected after movement of the readheads 60, 62 a predetermined distance), which if present causes an error flag to be set at step 358, and at step 360, the light sources 64, 68 turned on at step 344 are turned off.

If the above positioning routine is utilized, it may be modified by positioning one of the readheads 60, 62 relative to one of the calibration chips and (since the readheads 60, 62 are fixed relative to one another and since the calibration chips are also fixed relative to each other) assuming that the other readhead is properly positioned over its calibration chip.

Calibration Routine

The calibration routine 320 (FIG. 12) is performed after the detectors 66a–66d, 70a–70d of the readheads 60, 62 are positioned over the centers of the calibration chips, as described above. Referring to FIG. 12, at step 370 the detectors 66a–66d, 70a–70d are read with the light sources 64, 68 turned off. At step 372, the light sources 64, 68 are turned on, and at step 374 the detectors 66a–66d, 70a–70d are read with the light sources 64, 68 turned on.

If the detector readings taken at steps 370 and 374 are okay as determined at step 376 (e.g. if they are within expected ranges), the routine branches to step 378 where the readings are stored in memory. The magnitudes of the signals generated by the detectors 66a–66d, 70a–70d with the light sources 64, 68 off are referred to as "dark values," and the magnitudes of the signals generated by the detectors 66a–66d, 70a–70d with the light sources 64, 68 turned on are referred to as "calibration values." If the detector readings are not acceptable as determined at step 376, the routine branches to step 380 where an error flag is set.

Read Strip Routine

After the dark values and calibration values are determined as described above, the readheads 60, 62 are moved in a direction parallel to the lengths of the reagent strips 14 (or single strip) disposed at the two inspection locations so that the detectors 66a–66d generate illumination signals for each of the reagent pads 26 disposed along the length of each of the reagent strips 14.

This process may be accomplished in the particular manner described below in connection with FIG. 13, which could be used if the motor 58 used for the readhead positioning system described above is a stepping motor, which requires periodic inputs at well-defined intervals to keep the stepping motor running smoothly. The method of FIG. 13 takes a set of detector readings for each of the readheads 60, 62 each time the readheads 60, 62 move a predetermined distance, such as 0.017 of an inch.

Figure 13:
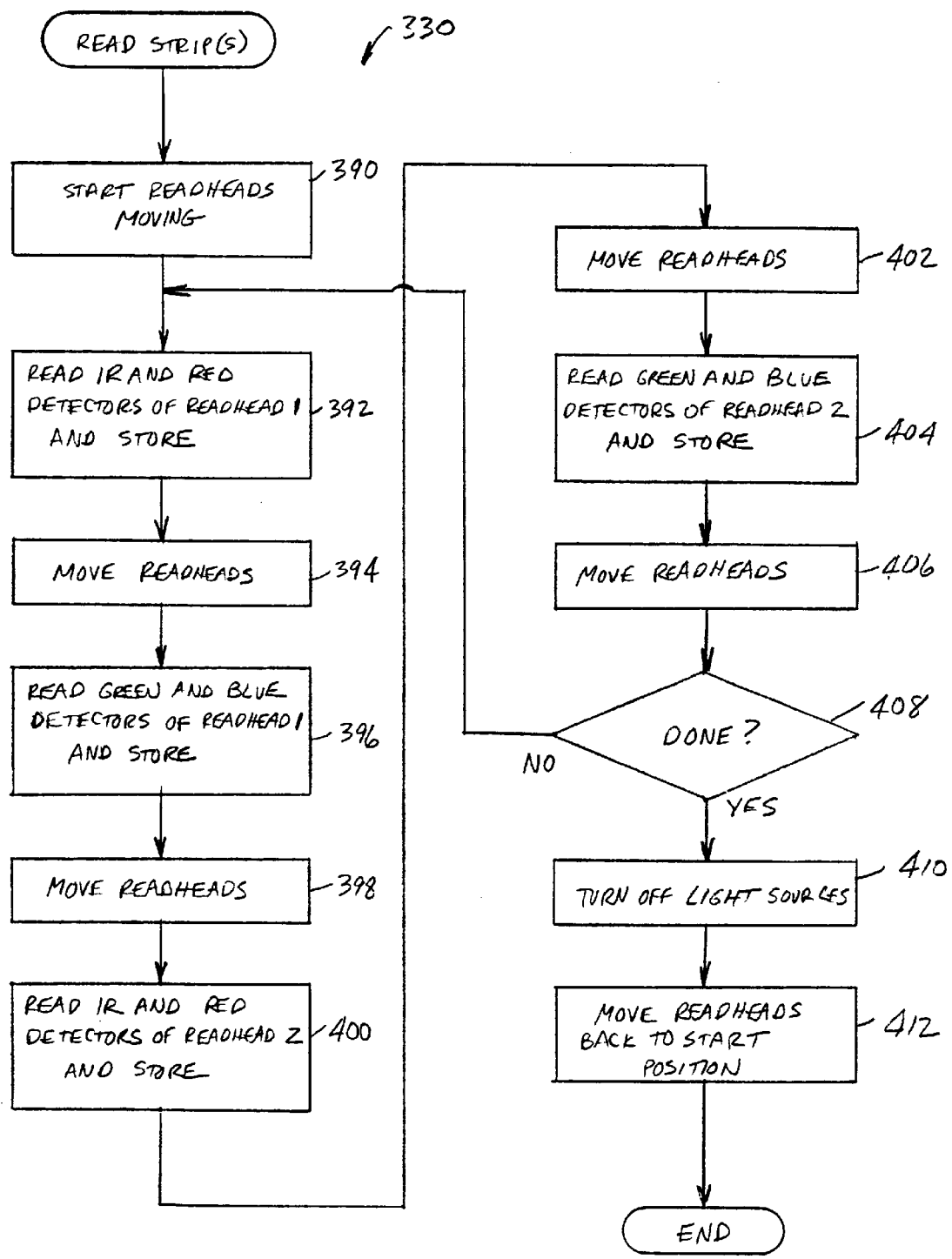
FIG. 13 is a flowchart of a read software routine performed during operation of the spectrophotometer.

Referring to FIG. 13, at step 390 the readheads 60, 62 are started moving, and when they reach a steady-state speed, at step 392 two of the four detectors 66a–66d for the readhead 60 are read and the signals are stored in memory. At step 394, another drive signal is transmitted to the motor 58 which drives the readheads 60, 62 to cause them to continue moving. At step 396, the other two detectors 66a–66d for the readhead 60 are read and the signals are stored in memory, and at step 398, another drive signal is transmitted to the motor 58 to cause the readheads 60, 62 to continue moving. Even steps 400–406 are performed to cause the detectors 70a–70d of the readhead 62 to be read and the associated signals to be stored in memory, and to drive the motor 58 for the readheads 60, 62.

At step 408, if not all of the desired readings have been taken (which may be determined by keeping track of the distance the readheads 60, 62 have travelled during the read routine 330), the routine branches back to step 392 to get another set of detector readings. If all of the readings have been taken, the routine branches to step 410, where the light sources 64, 68 are turned off, and then to step 412 where the readheads 60, 62 are moved back to their starting position (which is over the calibration chips).

The particular manner of generating the detector readings described in connection with FIG. 13 is not considered necessary to the invention, and other ways of generating the detector readings could be utilized.

Numerous other modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed and sought to be secured by Letters Patent is:

1. An apparatus for inspecting a reagent strip (14) having a plurality of reagent pads (26) after said reagent strip (14) has been contacted with a fluid sample, said apparatus comprising:

a conveyor system (80) adapted to move said reagent strip (14) from a first reagent strip inspection location to a second reagent strip inspection location;

a first readhead (60) associated with said first reagent strip inspection location and being adapted to optically inspect a plurality of said reagent pads (26) of said reagent strip (14), said first readhead (60) having a light source (64) and a light detector (66) associated therewith, said light source (64) being adapted to illuminate at least one of said reagent pads (26) of said reagent strip (14) at said first reagent strip inspection location and said light detector (66) being adapted to detect light from at least one of said reagent pads (26) of said reagent strip (14) when said reagent strip (14) is disposed at said first reagent strip inspection location and when said reagent strip (14) is illuminated by said light source (64);

a second readhead (62) associated with said second reagent strip inspection location and being adapted to optically inspect said reagent pads (26) of said reagent strip (14), said second readhead (62) having a light source (68) and a light detector (70) associated therewith, said light source (68) of said second readhead (62) being adapted to illuminate at least one of said reagent pads (26) of said reagent strip (14) at said second reagent strip inspection location and said light detector (70) of said second readhead (62) being adapted to detect light from at least one of said reagent pads (26) of said reagent strip (14) when said reagent strip (14) is disposed at said second reagent strip inspection location and when said reagent strip (14) is illuminated by said light source (68) of said second readhead (62); and a readhead positioning system (52, 54, 56) operatively coupled to at least one of said first and second readheads (60, 62), said readhead positioning system (52, 54, 56) being adapted to selectively position said one readhead (60) so that said one readhead (60) is automatically moved from a first position at which a first reagent pad (26) is inspected to a second position at which a second reagent pad (26) is inspected.

2. An apparatus as defined in claim 1 wherein said readhead positioning system (52, 54, 56) moves said one readhead (60, 62) in a direction parallel to the length of said reagent strip (14) so that said reagent pads (26) are optically inspected on a sequential basis.

3. An apparatus as defined in claim 1 wherein one of said light detectors (66, 70) comprises a plurality of detectors, each of said detectors being adapted to detect light of a different wavelength.

4. An apparatus as defined in claim 1 wherein said light detectors (66, 70) generate illumination signals and wherein said apparatus additionally comprises a memory (164) in which signals relating to said illumination signals are stored.

5. An apparatus as defined in claim 1 wherein said conveyor system (80) is adapted to simultaneously move a plurality of reagent strips (14).

6. An apparatus for inspecting reagent strips (14) each having a plurality of reagent pads (26) after said reagent strips (14) have been contacted with fluid samples, said apparatus comprising:

a conveyor system (80) adapted to move a plurality of said reagent strips (14) to a first reagent strip inspection location and a plurality of said reagent strips (14) to a second reagent strip inspection location;

a first readhead (60) associated with said first reagent strip inspection location and being adapted to optically inspect said reagent pads (26) of each of said reagent strips (14), said first readhead (60) having a light source (64) and a light detector (66) associated therewith, said light source (64) being adapted to illuminate one of said reagent pads (26) of a first of said reagent strips (14) at said first reagent strip inspection location and said light detector (66) being adapted to detect light from said one reagent pad (26) of said first reagent strip (14) when said first reagent strip (14) is disposed at said first reagent strip inspection location and when said first reagent strip (14) is illuminated by said light source (64);

a second readhead (62) associated with said second reagent strip inspection location and being adapted to optically inspect said reagent pads (26) of each of said reagent strips (14), said second readhead (62) having a light source (68) and a light detector (70) associated therewith, said light source (68) of said second readhead (62) being adapted to illuminate one of said reagent pads (26) of a second of said reagent strips (14) at said second reagent strip inspection location and said light detector (70) of said second readhead (62) being adapted to detect light from said one reagent pad (26) of said second reagent strip (14) when said second reagent strip (14) is disposed at said second reagent strip inspection location and when said second reagent strip (14) is illuminated by said light source (68) of said second readhead (62); and a readhead positioning system (52, 54, 56) operatively coupled to at least one of said first and second readheads (60, 62), said readhead positioning system (52, 54, 56) being adapted to selectively position said one readhead (60) so that said one readhead (60) is automatically moved from a first position at which a first reagent pad (26) is inspected to a second position at which a second reagent pad (26) is inspected.

7. An apparatus as defined in claim 6 wherein said readhead positioning system (52, 54, 56) automatically moves said one readhead (60, 62) in a direction parallel to the length of said reagent strip (14) so that said reagent pads (26) are optically inspected on a sequential basis.

8. An apparatus as defined in claim 6 wherein one of said light detectors (66, 70) comprises a plurality of detectors, each of said detectors being adapted to detect light of a different wavelength.

9. An apparatus as defined in claim 6 wherein said light detectors (66, 70) generate illumination signals and wherein said apparatus additionally comprises a memory (164) in which signals relating to said illumination signals are stored.

10. An apparatus as defined in claim 6 wherein said conveyor system (80) is adapted to simultaneously move a plurality of reagent strips (14).

11. An apparatus for inspecting reagent strips (14) after said reagent strips (14) having been contacted with a fluid sample, each of said reagent strips (14) having a length and a plurality of reagent pads (26) disposed along said length, said apparatus comprising:

a conveyor system (80) adapted to move a plurality of said reagent strips (14) to a first reagent strip inspection location and a plurality of said reagent strips (14) to a second reagent strip inspection location;

a first readhead (60) associated with said first reagent strip inspection location, said first readhead (60) having a light source (64) and a light detector (66) associated therewith, said light source (64) being adapted to illuminate a first of said reagent strips (14) at said first reagent strip inspection location and said light detector (66) being adapted to detect light from said first reagent strip (14) when said first reagent strip (14) is disposed at said first reagent strip inspection location and when said first reagent strip (14) is illuminated by said light source (64);

a second readhead (62) associated with said second reagent strip inspection location, said second readhead (62) having a light source (68) and a light detector (70) associated therewith, said light source (68) of said second readhead (62) being adapted to illuminate a second of said reagent strips (14) at said second reagent strip inspection location and said light detector (70) of said second readhead (62) being adapted to detect light from said second reagent strip (14) when said second reagent strip (14) is disposed at said second reagent strip inspection location and when said second reagent strip (14) is illuminated by said light source (68) of said second readhead (62); and a readhead positioning system (52, 54, 56) operatively coupled to said first and second readheads (60, 62), said readhead positioning system (52, 54, 56) being adapted to selectively position said first readhead (60) so that said first readhead (60) sequentially inspects a plurality of said reagent pads (26) disposed on said first reagent strip (14) when said first reagent strip (14) is disposed at said first inspection location, said readhead positioning system (52, 54, 56) being adapted to selectively position said second readhead (62) so that said second readhead (62) sequentially inspects a plurality of said reagent pads (26) disposed on said second reagent strip (14) when said second reagent strip (14) is disposed at said second inspection location.

12. An apparatus as defined in claim 11 wherein said positioning system (52, 54, 56) is adapted to move said first and second readheads (60, 62) together.

13. An apparatus as defined in claim 11 additionally comprising a memory (164) which stores signals relating to the amount of light detected by said light detectors (66, 70) associated with said first and second readheads (60, 62).

14. An apparatus as defined in claim 11 wherein one of said light detectors (66, 70) comprises a plurality of detectors, each of said detectors being adapted to detect light of a different wavelength.

15. An apparatus as defined in claim 11 wherein said conveyor system (80) is adapted to simultaneously move a plurality of said reagent strips (14) relative to said first and second readheads (60, 62).

16. A method of automatically processing a reagent strip (14) after said reagent strip (14) has been contacted with a fluid sample, said method comprising:

(a) automatically moving said reagent strip (14) to a first reagent strip inspection location;

(b) automatically moving a first readhead (60) relative to said reagent strip (14) when said reagent strip (14) is at said first inspection location;

(c) detecting light received from said reagent strip (14) while said reagent strip (14) is being illuminated at said first inspection location;

(d) storing signals relating to the amount of light detected from said reagent strip (14) when said reagent strip (14) was positioned at said first inspection location in a memory;

(e) automatically moving said reagent strip (14) to a second reagent strip inspection location;

(f) automatically moving a second readhead (62) relative to said reagent strip (14) when said reagent strip (14) is at said second inspection location;

(g) detecting light received from said reagent strip (14) while said reagent strip (14) is being illuminated at said second inspection location; and (h) storing signals relating to the amount of light detected from said reagent strip (14) when said reagent strip (14) was positioned at said second inspection location in a memory (164).

17. A method as defined in claim 16, wherein said reagent strip (14) has a plurality of reagent pads (26) disposed along its length, wherein said first readhead (60) is successively positioned over a plurality of said reagent pads (26) of said reagent strip (14), wherein light received from a plurality of said reagent pads (26) of said reagent strip (14) is detected while said reagent strip (14) is being illuminated at said first inspection location, and wherein signals relating to the amount of light detected from said plurality of reagent pads (26) of said reagent strip (14) when said reagent strip (14) was positioned at said first inspection location are stored in a memory (164).

* * * * *